United States Patent [19]

Kitching

[11] Patent Number: 6,125,690

[45] Date of Patent: Oct. 3, 2000

[54] DEVICE FOR TESTING OF DIESEL FUEL

[75] Inventor: John Stephen Kitching, Chester, United Kingdom

[73] Assignee: Shell Oil Company, Houston, Tex.

[21] Appl. No.: 09/143,176

[22] Filed: Aug. 28, 1998

[30] Foreign Application Priority Data

Sep. 12, 1997 [EP] European Pat. Off. .............. 97307080

[51] Int. Cl.⁷ .................................................. G01M 15/00
[52] U.S. Cl. .......................................... 73/35.02; 73/117.3
[58] Field of Search ................... 73/35.02, 116, 73/117.3, 117.2, 118.1

[56] References Cited

U.S. PATENT DOCUMENTS

| | | | |
|---|---|---|---|
| 4,443,787 | 4/1984 | Denk et al. . | |
| 4,640,251 | 2/1987 | Harada . | |
| 5,457,985 | 10/1995 | Cellier et al. ........................ | 73/35.02 |
| 5,505,079 | 4/1996 | Rossignol ............................. | 73/117.3 |
| 5,663,495 | 9/1997 | Allen et al. ........................... | 73/117.3 |
| 5,828,976 | 10/1998 | Fukuchi et al. ....................... | 73/117.3 |
| 5,864,775 | 1/1999 | Bradshaw et al. .................... | 73/117.3 |
| 5,875,411 | 2/1999 | Volkart et al. ........................ | 73/117.3 |
| 5,893,897 | 4/1999 | Volkart et al. ........................ | 73/117.3 |
| 5,951,618 | 9/1999 | Fukuchi et al. ....................... | 73/117.3 |

FOREIGN PATENT DOCUMENTS

| | | |
|---|---|---|
| 610118 | 8/1994 | European Pat. Off. . |
| 718599 | 6/1996 | European Pat. Off. . |
| 1270838 | 11/1962 | Germany . |
| 19520299 A1 | 12/1996 | Germany . |

OTHER PUBLICATIONS

International Search Report dated Mar. 1, 1999.

*Primary Examiner*—Eric S. McCall

[57] ABSTRACT

A device for generating a series of output signals in relation to a rotating output shaft of a diesel fuel test engine generating a series of engine signals, each engine signal occurring at a first angular orientation of the output shaft. Each output signal is generated at a second angular orientation of the output shaft. The device receives the series of engine signals, measures the angle of rotation of the output shaft relative to the occurrence of each engine signal, determines an angular interval between the first and second angular orientations of the output shaft, in the direction of rotation of the output shaft, and generates the output signal when the measured angle of rotation of the output shaft corresponds to the angular interval.

2 Claims, 2 Drawing Sheets

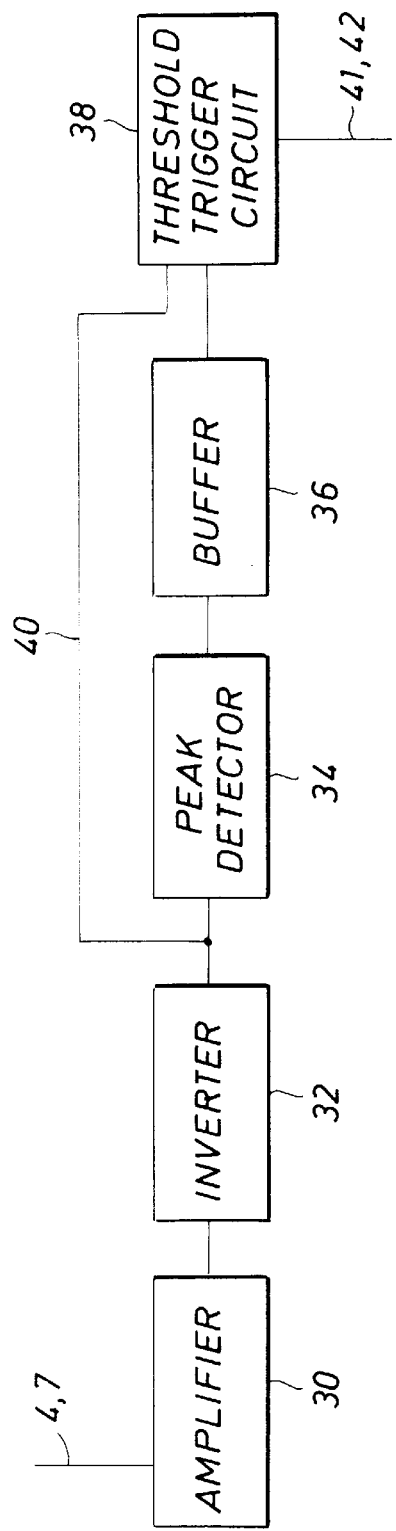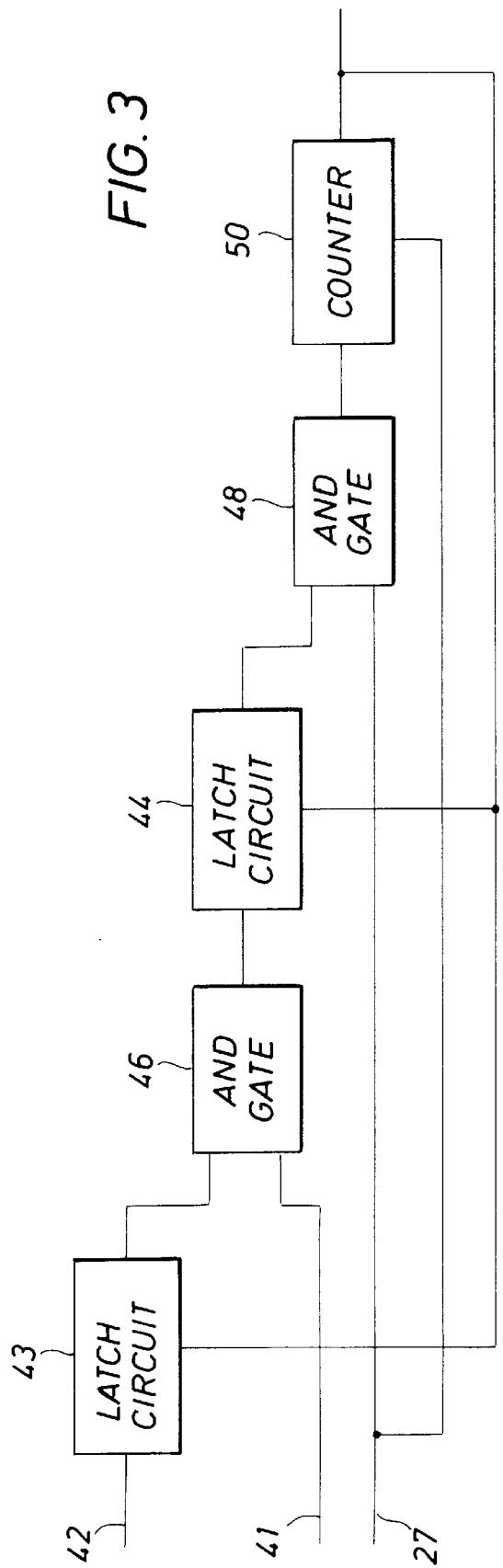

DEVICE FOR TESTING OF DIESEL FUEL

FIELD OF THE INVENTION

The present invention relates to a device for generating a series of output signals in relation to a rotating output shaft of a diesel fuel test engine having means for generating a series of engine signals, each engine signal occurring at a first angular orientation of the output shaft, each output signal being generated at a second angular orientation of the output shaft.

BACKGROUND OF THE INVENTION

A generally used characteristic parameter for indicating the quality of diesel fuel is the cetane number, which is, for a given engine compression rate, a measure of the time delay between injection and ignition of the fuel in the engine. A standard test engine, also referred to as CFR engine, is applied for such measurements. Apart from the time delay, the cylinder pressure is measured during a selected time interval of the compression stroke of the engine. The part of the engine cycle of interest generally is between 13° before top dead center (BTDC) and top dead center (TDC), and it is convenient to start data sampling at 30° BTDC compression.

In order to generate a trigger signal indicating 30° BTDC compression, it has already been proposed to apply an optical shaft encoder which generates crank angle degree markers and a reference pulse which is usually aligned, when fitted to the engine, with TDC. To only generate one pulse at 30° BTDC of the compression stroke of each engine cycle (two revolutions of the encoder shaft) the encoder is provided with internal gearing. The encoder then has to be carefully aligned with the engine so that the once per two revolutions signal occurs at 30° BTDC compression. This once per two revolutions signal could of course be set to occur anywhere in the engine cycle and it is only through careful alignment that it occurs at the required 30° BTDC compression. A drawback of such system is the requirement for a non-standard encoder. Moreover exact alignment of the encoder with the engine is difficult to achieve or to maintain.

OBJECT OF THE INVENTION

It is an object of the invention to provide an improved device for generating a series of output signals representing a selected angular orientation of an output shaft of a diesel fuel test engine, which device obviates the need for a non-standard encoder.

DESCRIPTION OF THE INVENTION

In accordance with the invention there is provided a device for generating a series of output signals in relation to a rotating output shaft of a diesel fuel test engine having means for generating a series of engine signals, each engine signal occurring at a first angular orientation of the output shaft, each output signal being generated at a second angular orientation of the output shaft, the device comprising:
  an input for receiving the series of engine signals;
  means for measuring the angle of rotation of the output shaft relative to the occurrence of each engine signal;
  means for determining an angular interval between said first and second angular orientations of the output shaft, in the direction of rotation of the output shaft; and
  means for generating said output signal when the measured angle of rotation of the output shaft corresponds to said angular interval.

By using each engine signal as a reference point for the angular rotation of the output shaft, the need for a non-standard encoder which must exactly aligned with the output shaft, is eliminated. Upon the occurrence of the engine signal the rotation angle is measured until the angular interval (which is determined by the difference between the first angular orientation and the second angular orientation, in the direction of rotation) is reached, following which the output signal is generated. The output signal serves, for example, as a trigger point for the start of data sampling.

Suitably the means for measuring the angular rotation comprises an encoder for generating a series of pulse signals at selected angular increments of rotation of the output shaft, and a counter for counting the pulse signals from the occurrence of the engine signal.

Preferably the means for generating the output signal is adapted to generate the output signal when the counter has counted the number of pulse signals corresponding to said angular interval.

A preferred primary engine signal represents the top dead center (TDC) compression of the engine.

In order to arm the counter prior to TDC compression, suitably said series of engine signals forms a series of primary engine signals, and the device further comprises means for receiving a series of secondary engine signals from the engine, each secondary engine signal representing the start of fuel injection into the engine before a combustion stroke thereof, said means for receiving the secondary engine signals being connected to the counter so as to arm the counter upon receiving each secondary signal.

BRIEF DESCRIPTION OF THE DRAWINGS

The invention will be described hereinafter by way of example and in more detail, and with reference to the drawings in which:

FIG. 2 shows a block diagram of a signal conditioning unit used in the electronic circuit of FIG. 1; and FIG. 3 shows a block diagram of an output generator used in the electronic circuit of FIG. 1.

DETAILED DESCRIPTION OF THE DRAWINGS

Figure 1:
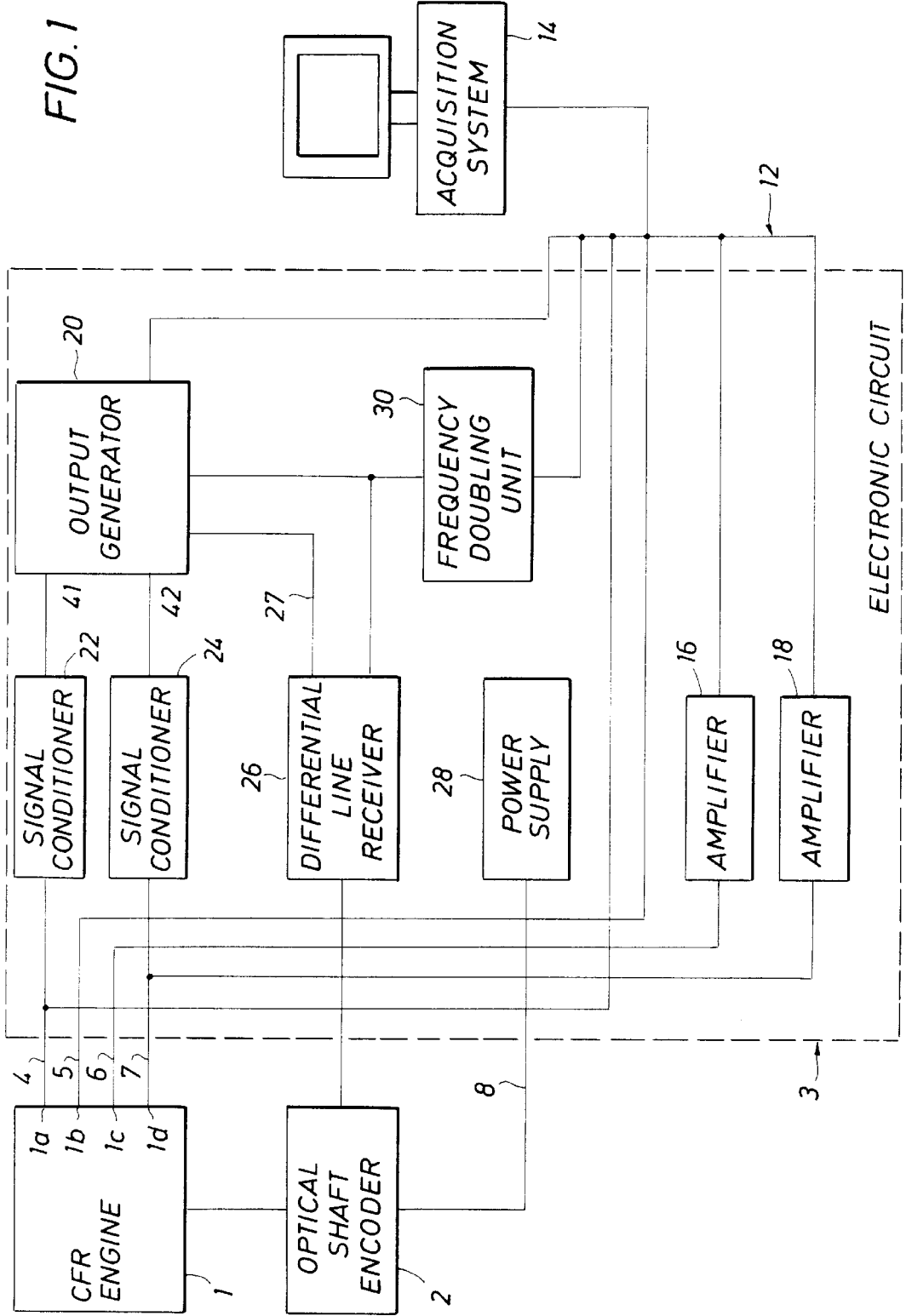
FIG. 1 shows a block diagram of an electronic circuit applied in an embodiment of the device according to the invention.

In FIG. 1 reference numeral 1 indicates a CFR engine 1 for conducting cetane number measurements of diesel fuel, reference numeral 2 indicates an optical shaft encoder attached to the crankshaft of the engine 1, and reference numeral 3 indicates an electronic circuit receiving input signals from the engine 1 and from the shaft encoder 2.

The engine is provided with transducers 1a, 1b, 1c, 1d for transmitting respective signal series: top dead center (TDC) compression, 12.5° before TDC (BTDC), cylinder pressure, and fuel injection. The shaft encoder 2 generates two differential out of phase pulse trains of 1440 pulses per revolution of the crankshaft each. Each pulse generated by the shaft encoder 2 can be seen as a crank angle degree marker (CDM) pulse.

The electronic circuit 3 has the following input ports: a TDC signal port 4, a 12.5° BTDC signal port 5, a pressure signal port 6, an injection signal port 7, and a port 8 for the shaft encoder pulse trains. The engine signals are delivered to these input ports, and from there to an output port 12 which is connected to a data acquisition system 14. The pressure signals and the injection signals are first amplified by respective amplifiers 16, 18 before being delivered to the output port 12. Furthermore, the TDC signals and the injection signals are delivered from the input ports 4, 7 to respective signal conditioners 22, 24 which are described in more detail below. The conditioned signals are provided to an output generator 20. To reduce the influence of noise in the pulse trains from the shaft encoder, the pulse trains are combined by a differential line receiver 26 to produce a TTL pulse train which is delivered to the output pulse generator 20 via port 27. Furthermore in FIG. 1 reference numeral 28 indicates a power supply for the shaft encoder 2, and reference numeral 30 indicates a unit for doubling of the frequency of the shaft encoder pulse trains to 2880 pulses per revolution as required for the acquisition system 14.

In FIG. 2 is shown a block diagram of each one of the signal conditioners 22, 24. The signal conditioner 22, 24 receives input signal at input 4, 7, which signal is amplified by amplifier 30 and inverted by inverter 32. In order that the output is generated at the same point relative to the peak of the input signal, the peak of the signal is detected by peak detector 34. The signal is subsequently buffered in buffer 36 before being fed to a threshold trigger circuit 38 which allows the trigger point for the generation of the output signal to be set relative to the peak of the signal received from inverter 32 via line 40. A TTL output signal is then generated at port 41 of TDC signal conditioner 22 and at port 42 of injection signal conditioner 24, the TTL signals being fed to the output generator 20.

Referring to FIG. 3 there is shown a block diagram of output generator 20 which is set up to provide an output signal at 30° BTDC compression. The output generator 20 has two latch circuits 43, 44, two AND gates 46, 48 and a counter 50. The latch circuit 43 receives the conditioned injection signal from port 42 and delivers a signal to AND gate 44 which also receives the conditioned TDC signal from port 41. AND gate 46 delivers an output signal to latch circuit 44 which in turn provides an output signal to AND gate 48. Further, the combined pulse train signal from the differential line receiver 26 is delivered via port 27 to AND gate 48 which delivers a signal to counter 50. The counter 50 starts to count the pulses delivered by the shaft encoder once the circuit has seen an injection pulse followed by a TDC pulse. It then counts the required number of pulses until 30° BTDC of the next compression stroke, and then gives an output signal which is used to reset the latch circuits 43, 44 ready for the next cycle. The counter 50 is reset once the required number of pulses has been counted.

Normal operation of the device schematically shown in FIGS. 1–3 is as follows. During running of the test engine 1 conditioned injection signal from conditioner 24 is used to arm counter 50 in order to distinguish a compression stroke of the engine 1 from an exhaust stroke thereof. Thus the counter 50 begins to count CDM pulses after having received an injection signal followed by a TDC signal. The counter 50 counts the required number of pulses and then outputs a signal at 30° BTDC of the next compression stroke. The counter 50 is then reset by the following CDM pulse whereafter the process repeats itself. The 30° BTDC is used to initiate measurement of the time interval between injection and ignition, i.e. the ignition delay period, which forms a measure for the cetane number of the diesel fuel being tested.

What is claimed is:

1. A device for generating a series of output signals in relation to a rotating output shaft of a diesel fuel test engine having means for generating a series of engine signals, each engine signal occurring at a first angular orientation of the output shaft, each output signal being generated at a second angular orientation of the output shaft, the device comprising:

an input for receiving the series of engine signals;

means for measuring the angle of rotation of the output shaft relative to the occurrence of each engine signal;

means for determining an angular interval between said first and second angular orientations of the output shaft, in the direction of rotation of the output shaft;

means for generating said output signal when the measured angle of rotation of the output shaft corresponds to said angular interval;

wherein each engine signal occurs at top dead center (TDC) compression of the engine; and, wherein said series of engine signals forms a series of primary engine signals, the device further comprising means for receiving a series of secondary engine signals from the engine, each secondary engine signal representing the start of fuel injection into the engine before a combustion stroke thereof, said means for receiving the secondary engine signals being connected to the counter so as to arm the counter upon receiving each secondary signal.

2. A device for generating a series of output signals in relation to a rotating output shaft of a diesel fuel test engine having means for generating a series of engine signals, each engine signal occurring at a first angular orientation of the output shaft, each output signal being generated at a second angular orientation of the output shaft, the device comprising:

an input for receiving the series of engine signals;

means for measuring the angle of rotation of the output shaft relative to the occurrence of each engine signal;

means for determining an angular interval between said first and second angular orientations of the output shaft, in the direction of rotation of the output shaft;

wherein the diesel fuel has a cetane number and the test engine has a cylinder pressure;

the device is used to determine the cetane number of the diesel fuel, and wherein each output signal is used to initiate measuring of the cylinder pressure of the test engine.

* * * * *